(12) United States Patent
Park et al.

(10) Patent No.: US 9,393,339 B2
(45) Date of Patent: Jul. 19, 2016

(54) ANTIMICROBIAL FILTER ADOPTING OPTICAL FIBERS AND AIR CLEANER COMPRISING SAME

(71) Applicant: KOREA INSTITUTE OF ENERGY RESEARCH, Daejeon (KR)

(72) Inventors: Hyun-Seol Park, Daejeon (KR); Jeong-Gu Yeo, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 0 days.

(21) Appl. No.: 14/360,536

(22) PCT Filed: May 8, 2013

(86) PCT No.: PCT/KR2013/003989
§ 371 (c)(1),
(2) Date: May 23, 2014

(87) PCT Pub. No.: WO2013/168985
PCT Pub. Date: Nov. 14, 2013

(65) Prior Publication Data
US 2015/0075384 A1 Mar. 19, 2015

(30) Foreign Application Priority Data

May 8, 2012 (KR) .......... 10-2012-0048761
May 16, 2012 (KR) .......... 10-2012-0051866
May 16, 2012 (KR) .......... 10-2012-0051867

(51) Int. Cl.
*A61L 9/20* (2006.01)
*B01D 53/88* (2006.01)

(52) U.S. Cl.
CPC ............. *A61L 9/20* (2013.01); *B01D 53/885* (2013.01); *B01D 2239/0442* (2013.01);
(Continued)

(58) Field of Classification Search
CPC ........... B01D 53/885; B01D 2255/802; B01D 2257/91

USPC ................ 96/224, 226; 55/524
See application file for complete search history.

(56) References Cited

U.S. PATENT DOCUMENTS

| | | | | |
|---|---|---|---|---|
| 6,048,499 A | * | 4/2000 | Hirayama | A61L 9/18 422/121 |
| 2010/0029157 A1 | | 2/2010 | Brochier et al. | |
| 2011/0171080 A1 | * | 7/2011 | Lo | A61L 2/088 422/186.3 |

FOREIGN PATENT DOCUMENTS

| | | |
|---|---|---|
| CN | 101543785 A | 9/2009 |
| CN | 201350377 | 11/2009 |

(Continued)

OTHER PUBLICATIONS

Office Action dated Aug. 20, 2013 issued for Korean patent application No. 10-2012-0051866.
(Continued)

*Primary Examiner* — Robert Clemente
*Assistant Examiner* — Karla Hawkins
(74) *Attorney, Agent, or Firm* — Michael J. Feigin, Esq.; Feigin & Fridman

(57) ABSTRACT

The present invention relates to an antimicrobial filter adopting optical fibers and to an air cleaner comprising the same. More particularly, the present invention relates to an antimicrobial filter using optical fibers and to an air cleaner comprising the same, in which ultraviolet rays, visible light or natural light is emitted directly through the surface of optical fibers contained in a filtering material, thus effectively killing, in a short time, microorganisms collected in the filtering material, such as bacteria, fungi, or viruses, which are harmful to the human body. Furthermore, a photocatalyst may be coated on the surface of the filtering material to achieve an improved sterilization effect. Thus, the deterioration of the sterilization effect caused by dust particles being continuously collected at the surface of filter fiber, which are disadvantages of existing antimicrobial filters, can be overcome.

9 Claims, 17 Drawing Sheets

(52) U.S. Cl.
CPC ...... *B01D 2255/802* (2013.01); *B01D 2257/91* (2013.01); *B01D 2258/06* (2013.01); *B01D 2259/802* (2013.01); *B01D 2259/804* (2013.01)

(56) References Cited

FOREIGN PATENT DOCUMENTS

| | | | |
|---|---|---|---|
| JP | 11290695 | A | 10/1999 |
| JP | 2000051342 | A | 2/2000 |
| JP | 2003265967 | A | 9/2003 |
| JP | 2005305333 | A | 11/2005 |
| JP | 2010513737 | A | 4/2010 |
| JP | 2011056155 | A | 3/2011 |
| KR | 1020060092169 | | 8/2006 |
| KR | 100922254 | | 10/2009 |

OTHER PUBLICATIONS

Office Action dated Jan. 30, 2015 issued for Chinese patent application No. 201380004511.4.

* cited by examiner

ANTIMICROBIAL FILTER ADOPTING OPTICAL FIBERS AND AIR CLEANER COMPRISING SAME

TECHNICAL FIELD

The present invention relates to an antimicrobial filter using optical fibers and an air cleaner comprising the same, and more particularly, to a technique for killing harmful microorganisms which are collected by a filter when purifying air using the filter. Among antimicrobial and disinfecting techniques including treatment using heat, UV light, radiation, chemicals, etc., the present invention pertains to an antimicrobial technology using UV light.

BACKGROUND ART

Useful in air purification, a high-efficiency filter is capable of effectively collecting almost all harmful microorganisms. However, microorganisms collected by the filter may live for a long period of time, and may even proliferate. To solve such problems, a variety of antimicrobial filters have been developed.

As such, antimicrobial techniques for coating the surface of a filter with an antimicrobial material have been employed, especially antimicrobial techniques for a filter for air purification wherein ion clusters are generated at the front of the filter and ions are thus attached to microorganisms collected by the filter to thereby kill the microorganisms. However, dust may function as a protection barrier for microorganisms due to continuous accumulation thereof on the filter, making it impossible to effectively kill the harmful microorganisms by the conventional techniques.

Also, as illustrated in FIG. 1, attempts have been made to irradiate a UV light source 3 onto the surface of a filter 1 so as to kill microorganisms 2, but the UV light 3 is irradiated only onto the surface of the filter 1 and cannot kill the collected microorganisms 2 in the filter 1.

DISCLOSURE

Technical Problem

Accordingly, the present invention has been made keeping in mind the above problems encountered in the related art, and an object of the present invention is to provide an antimicrobial filter using an optical fiber-mixed nonwoven fabric and an air cleaner comprising the same, wherein to kill harmful microorganisms such as bacteria, fungi, viruses, etc., UV light, visible light or natural light is irradiated to the inside of the filter through the surface of optical fibers of the filter, so that harmful microorganisms collected onto the surface of the fibers of the filter are killed, thereby overcoming drawbacks of conventional antimicrobial filters including deterioration of antimicrobial functions and low antimicrobial performance, as caused by continuously collecting dust particles by the filter.

Technical Solution

In order to accomplish the above object, the present invention provides an antimicrobial filter using optical fibers, comprising a filtration material including one or more optical fibers in which a portion of a light source, which is received from one end of the optical fibers and travels in a longitudinal direction, is emitted through the surface of the optical fibers, the filtration material having a porous structure with air permeability in a thickness direction and filtering particulate matter in air; a light source unit for irradiating a light source to one end of the optical fibers of the filtration material; and a power supply connected to the light source unit to apply power so as to operate the light source, and also provides an air cleaner comprising the antimicrobial filter using optical fibers as above.

In addition, the present invention provides an antimicrobial filter using optical fibers, comprising a filtration material including an optical fiber layer composed exclusively of optical fibers in which a light source, which is received from one end of the optical fibers and travels in a longitudinal direction, is emittable through the surface of the optical fibers, and a filtration layer for filtering particulate matter in air without including the optical fibers; a light source unit for irradiating a light source to one end of the optical fibers of the optical fiber layer; and a power supply connected to the light source unit to apply power so as to operate the light source.

In addition, the present invention provides an antimicrobial filter using optical fibers, comprising a filtration material including an optical fiber layer composed exclusively of optical fibers in which a light source, which is received from one end of the optical fibers and travels in a longitudinal direction, is emittable through the surface of the optical fibers, and a filtration layer for filtering particulate matter in air without including the optical fibers; a light source unit for irradiating a light source to one end of the optical fibers of the optical fiber layer; a connector for connecting one end of the optical fibers of the optical fiber layer and the light source unit; and a power supply connected to the light source unit to apply power so as to operate the light source.

In addition, the present invention provides an antimicrobial filter using optical fibers, comprising an optical fiber-mixed nonwoven fabric formed by irregularly mixing general fibers with optical fibers in which a light source, which is received from one end of the optical fibers and travels in a longitudinal direction, is emittable through the surface of the optical fibers; a light source unit for irradiating a light source to one end of the optical fiber-mixed nonwoven fabric; and a power supply connected to the light source unit to apply power so as to operate the light source.

In addition, the present invention provides an antimicrobial filter using optical fibers, comprising a filtration material including an optical fiber-mixed nonwoven fabric formed by mixing general fibers with optical fibers in which a light source, which is received from one end of the optical fibers and travels in a longitudinal direction, is emittable through the surface of the optical fibers, and a filtration layer formed so as to be stacked on the optical fiber-mixed nonwoven fabric and for filtering particulate matter in air without including the optical fibers; a light source unit for irradiating a light source to one end of the optical fiber-mixed nonwoven fabric; and a power supply connected to the light source unit to apply power so as to operate the light source.

ADVANTAGEOUS EFFECTS

According to the present invention, an antimicrobial filter using optical fibers and an air cleaner comprising the same can be advantageous because UV light, visible light or natural light is directly irradiated to the inside of the filter through surface emission of the optical fibers, and thereby collected microorganisms in the filter, such as bacteria, fungi, viruses, etc., which are harmful to human bodies, can be effectively killed within a short period of time; and also, the filtration material can be coated with a photocatalyst to thus increase disinfecting effects. Therefore, the antimicrobial filter is effective at overcoming problems of conventional antimicrobial filters including deterioration of disinfecting effects as caused by continuously collecting dust particles to the fiber surface of the filter.

Figure 1:
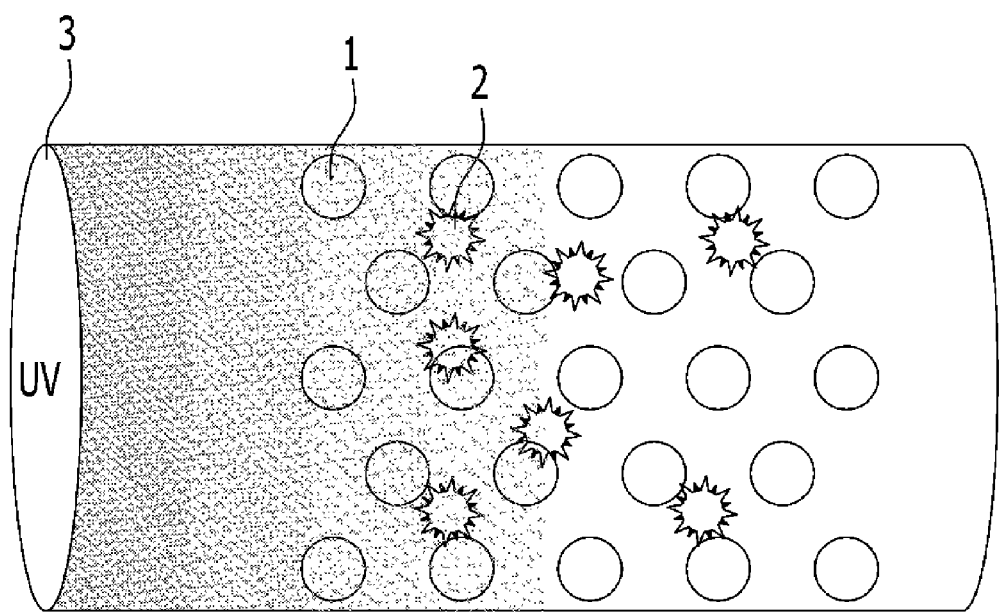
FIG. 1 is a schematic view illustrating a conventional filter.

| <Description of the Reference Numerals in the Drawings> | |
|---|---|
| 10: filtration material | 20: optical fiber |
| 21: core part | 22: clad part |
| 23: light emission part | 30: light source unit |
| 31, 41: PCB | 40: power supply |
| 50: optical fiber layer | 60: filtration layer |
| 70: connector | 100: antimicrobial filter |
| 100A: antimicrobial filter using optical fiber layer | |
| 100B: antimicrobial filter using optical fiber-mixed nonwoven fabric | |
| 110: pretreatment filter | 120: adsorption filter |
| 130: air blower | 140: charging device |
| 141: ground electrode | 142: discharge electrode |
| 150: high-performance filter | 160: duct case |
| 161: inlet | 162: outlet |
| 200, 200A, 200B: air cleaner | |

MODE FOR INVENTION

The present invention has the following features to achieve the above purpose.

According to the present invention, an antimicrobial filter using optical fibers comprises a filtration material including one or more optical fibers wherein a portion of a light source, which is received from one end of the optical fibers and travels in a longitudinal direction, is emitted through the surface of the optical fibers, the filtration material having a porous structure with air permeability in a thickness direction and filtering particulate matter in air; a light source unit for irradiating a light source to one end of the optical fibers of the filtration material; and a power supply connected to the light source unit to apply power so as to operate the light source. In addition, the present invention addresses an air cleaner including the antimicrobial filter using optical fibers as above.

According to the present invention, an antimicrobial filter using an optical fiber layer comprises a filtration material including an optical fiber layer composed exclusively of optical fibers in which a light source, which is received from one end of the optical fibers and travels in a longitudinal direction, is emittable through the surface of the optical fibers, and a filtration layer for filtering particulate matter in air without including the optical fibers; a light source unit for irradiating a light source to one end of the optical fibers of the optical fiber layer; and a power supply connected to the light source unit to apply power so as to operate the light source. In addition, an antimicrobial filter using an optical fiber layer according to the present invention comprises a filtration material including an optical fiber layer composed exclusively of optical fibers in which a light source, which is received from one end of the optical fibers and travels in a longitudinal direction, is emittable through the surface of the optical fibers, and a filtration layer for filtering particulate matter in air without including the optical fibers; a light source unit for irradiating a light source to one end of the optical fibers of the optical fiber layer; a connector for connecting one end of the optical fibers of the optical fiber layer and the light source unit; and a power supply connected to the light source unit to apply power so as to operate the light source.

According to the present invention, an antimicrobial filter using an optical fiber-mixed nonwoven fabric comprises an optical fiber-mixed nonwoven fabric formed by irregularly mixing general fibers with optical fibers in which a light source, which is received from one end of the optical fibers and travels in a longitudinal direction, is emittable through the surface of the optical fibers; a light source unit for irradiating a light source to one end of the optical fiber-mixed nonwoven fabric; and a power supply connected to the light source unit to apply power so as to operate the light source. In addition, an antimicrobial filter using an optical fiber-mixed nonwoven fabric according to the present invention comprises a filtration material including an optical fiber-mixed nonwoven fabric formed by mixing general fibers with optical fibers in which a light source, which is received from one end of the optical fibers and travels in a longitudinal direction, is emittable through the surface of the optical fibers, and a filtration layer formed so as to be stacked on the optical fiber-mixed nonwoven fabric and for filtering particulate matter in air without including the optical fibers; a light source unit for irradiating a light source to one end of the optical fiber-mixed nonwoven fabric; and a power supply connected to the light source unit to apply power so as to operate the light source.

The present invention having the above features will be able to be more clearly explained through preferred embodiments thereof.

Hereinafter, a detailed description will be given of preferred embodiments of the present invention with reference to the appended drawings. Prior thereto, the terminologies or words used in the description and the claims of the present invention are not construed limitedly as typical or dictionary meanings and should be interpreted as the meanings and concepts of the invention in keeping with the scope of the invention based on the principle that the inventors can appropriately define the terms in order to describe the invention in the best way.

Therefore, the examples described in the present specification and the constructions illustrated in the drawings are merely preferred embodiments of the present invention, and do not represent all of the technical ideas of the present invention, and thus, it is to be understood that a variety of equivalents and modifications being able to be substituted therefor may be provided at the point of time of the present invention being filed.

Figure 2:
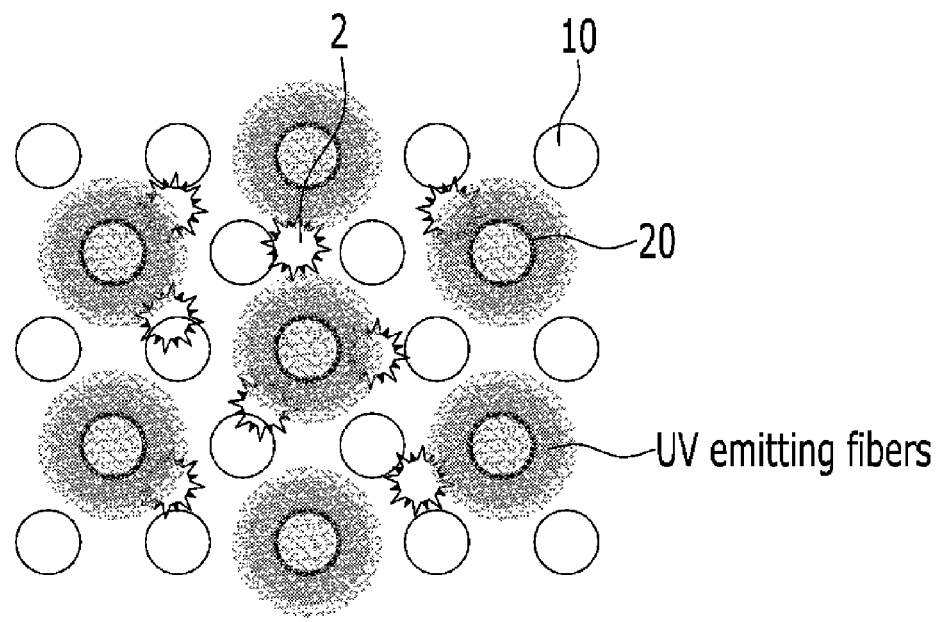
FIG. 2 is a cross-sectional view illustrating an antimicrobial filter using optical fibers according to an embodiment of the present invention.
Figure 3:
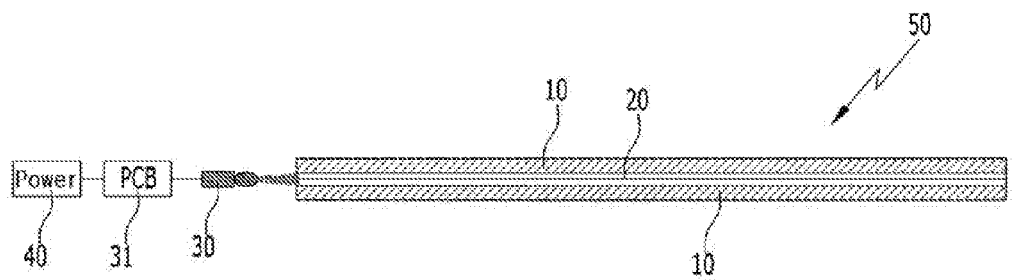
FIG. 3 is a side view illustrating an antimicrobial filter using optical fibers according to an embodiment of the present invention.
Figure 4:
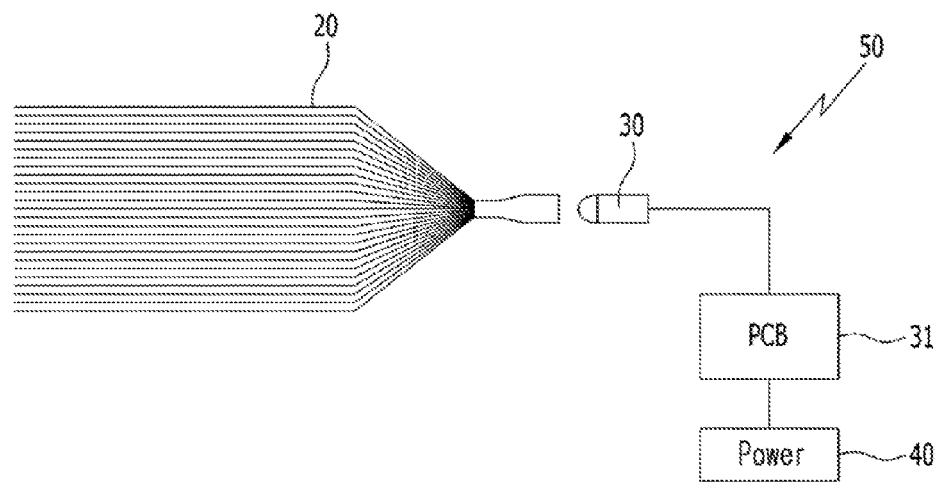
FIG. 4 is a schematic view illustrating an antimicrobial filter using optical fibers according to an embodiment of the present invention.
Figure 5:
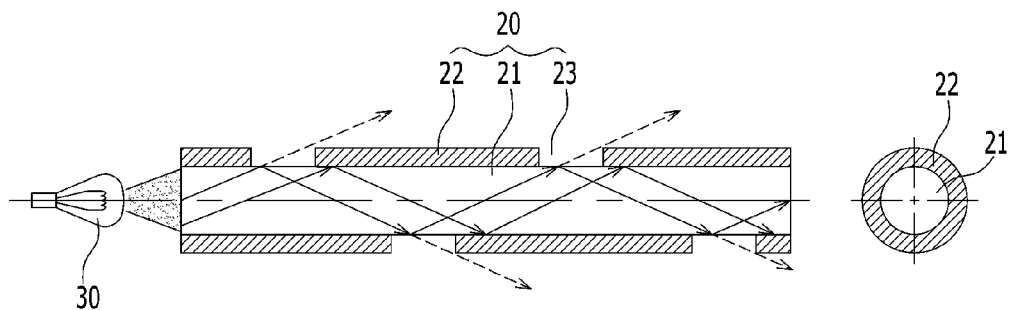
FIG. 5 is a side cross-sectional view illustrating optical fibers according to an embodiment of the present invention.

FIG. 2 is a cross-sectional view illustrating an antimicrobial filter using optical fibers according to an embodiment of the present invention, FIG. 3 is a side view illustrating an antimicrobial filter using optical fibers according to an embodiment of the present invention, FIG. 4 is a schematic view illustrating an antimicrobial filter using optical fibers according to an embodiment of the present invention, and FIG. 5 is a side cross-sectional view illustrating optical fibers according to an embodiment of the present invention.

As illustrated in FIGS. 2 to 5, the antimicrobial filter 100 using optical fibers according to the present invention comprises a filtration material 10 including one or more optical fibers in which a portion of a light source, which is received from one end of the optical fibers and travels in a longitudinal direction, is emitted through the surface of the optical fibers, the filtration material having a porous structure with air permeability in a thickness direction and filtering particulate matter in air, a light source unit 30 for irradiating a light source to one end of the optical fibers of the filtration material 10, and a power supply 40 connected to the light source unit 30 to apply power so as to operate the light source.

As illustrated in FIGS. 2 and 3, the filtration material 10 functions to filter particulate matter (bacteria, fungi, viruses, etc.) in air and has a porous structure, and is typically provided in the form of woven fabric or nonwoven fabric.

As illustrated in FIGS. 2 to 5, the optical fibers 20 are formed so as to be contained in the filtration material 10. When the light source of the light source unit 30 is irradiated to one end of the optical fibers 20, it is transferred in a longitudinal direction of the optical fibers 20, and light transferred through the core part 21 of the optical fibers 20 is emitted through the surface of the clad part 22, thus effectively killing harmful microorganisms 2 collected by the filtration material 10 or the optical fibers 20.

The optical fibers 20 include a core part 21 extending in a longitudinal direction and having a refractive index higher than that of air, a clad part 22 having a refractive index lower than that of the core part and formed around the core part 21, and a light emission part 23 formed by partially removing the clad part.

Also, when forming the core part 21 and the clad part 22 of the optical fibers 20, light may be emitted through the surface of the clad part 22 by combining materials having various refractive index values or by adjusting the thickness of the clad part 22.

The optical fibers 20 may be formed of a plastic material, and the light emission part 23 is uniformly distributed on the surface of the optical fibers 20.

The optical fibers 20 have a cross-sectional diameter of 2 mm or less to ensure flexibility, and the diameter thereof is illustratively set to 1 mm in the present invention.

The filtration material 10 including the optical fibers 20 is coated with a photocatalyst to enhance disinfecting effects.

As illustrated in FIGS. 3 and 4, the light source unit 30 is a device for producing a light source which is to be irradiated to one end of the optical fibers 20 of the filtration material 10. Although a variety of devices may be provided, in the present invention, the light source unit 30 is connected to PCB (Printed Circuit Board) 31 so as to control the light source. The light source irradiation by the light source unit 30 is typically known and functions and structures thereof are not additionally described.

Herein, the light source may be any one selected from among visible light, UV light and natural light, and one or more of them may be simultaneously used.

Even when the irradiation time of the light source is set to within 1 hr per day to prevent breakage of the polymer of the filtration material due to the long-term use of the light source, sufficient disinfecting effects may be obtained.

As illustrated in FIGS. 3 and 4, the power supply 40 is connected to the light source unit 30 to apply power so as to operate the light source, and is connected to the PCB 31 so that the produced power is supplied to the PCB 31.

Figure 6:
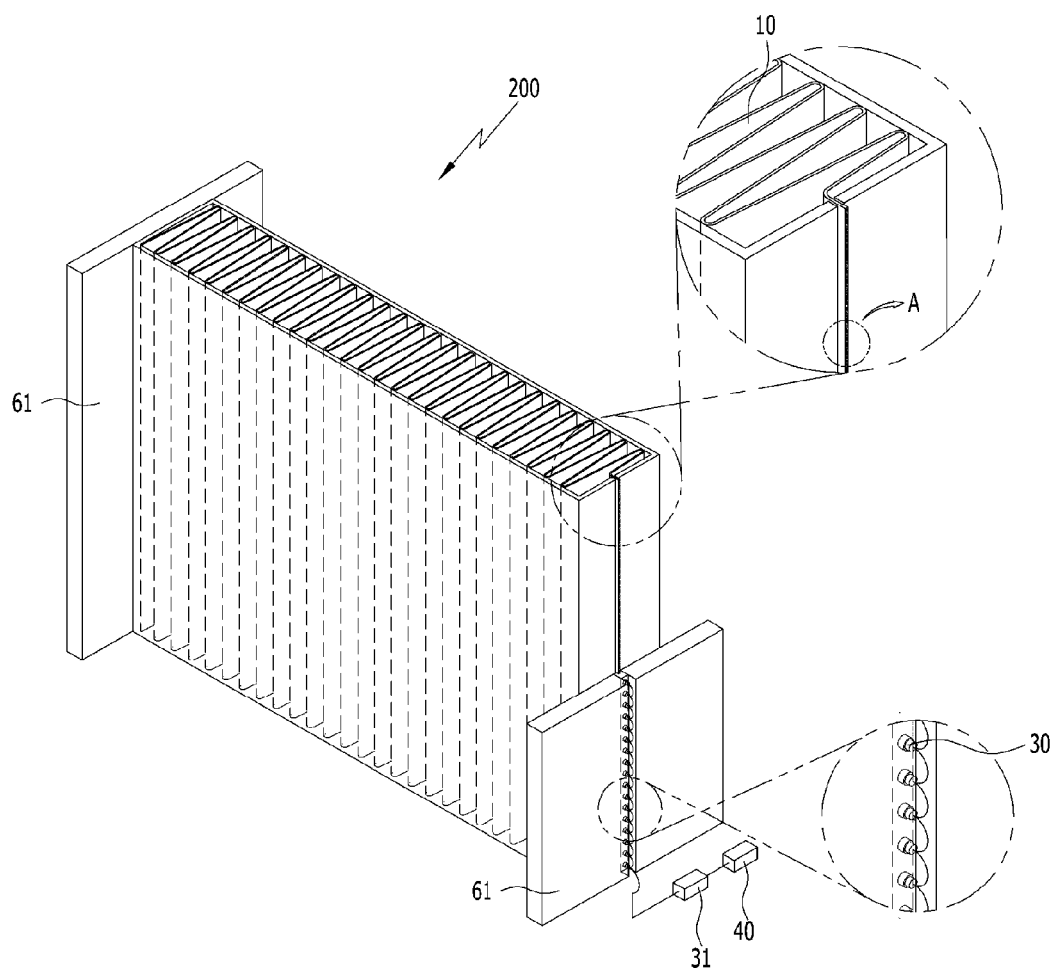
FIG. 6 is a schematic view illustrating an air cleaner including the antimicrobial filter according to an embodiment of the present invention.
Figure 7:
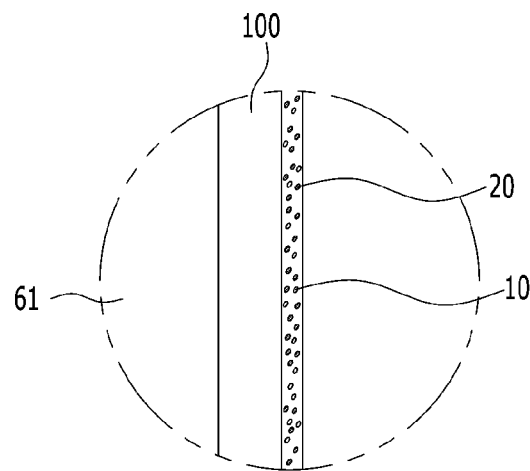
FIG. 7 is an enlarged view of Portion A of FIG. 6.

FIG. 6 is a schematic view illustrating an air cleaner including the antimicrobial filter using optical fibers according to an embodiment of the present invention, and FIG. 7 is an enlarged view of Portion A of FIG. 6.

As illustrated in FIGS. 6 and 7, the air cleaner 200 according to the present invention is an air cleaner 200 including the antimicrobial filter 100 using the optical fibers 20 as described above, wherein the antimicrobial filter 100 is inserted into the duct case 160 of the air cleaner 200, and the light source unit 30 and the power supply 40 are provided at one end of the antimicrobial filter 100, that is, the lateral side of the duct case 160 of the air cleaner 200.

The antimicrobial filter 100 of the air cleaner 200 is provided in the form of a pleated filter having a "∧ ∧ ∧" shape in order to increase the filtration area. This is merely illustrative, and various design modifications thereof are possible.

Figure 8:
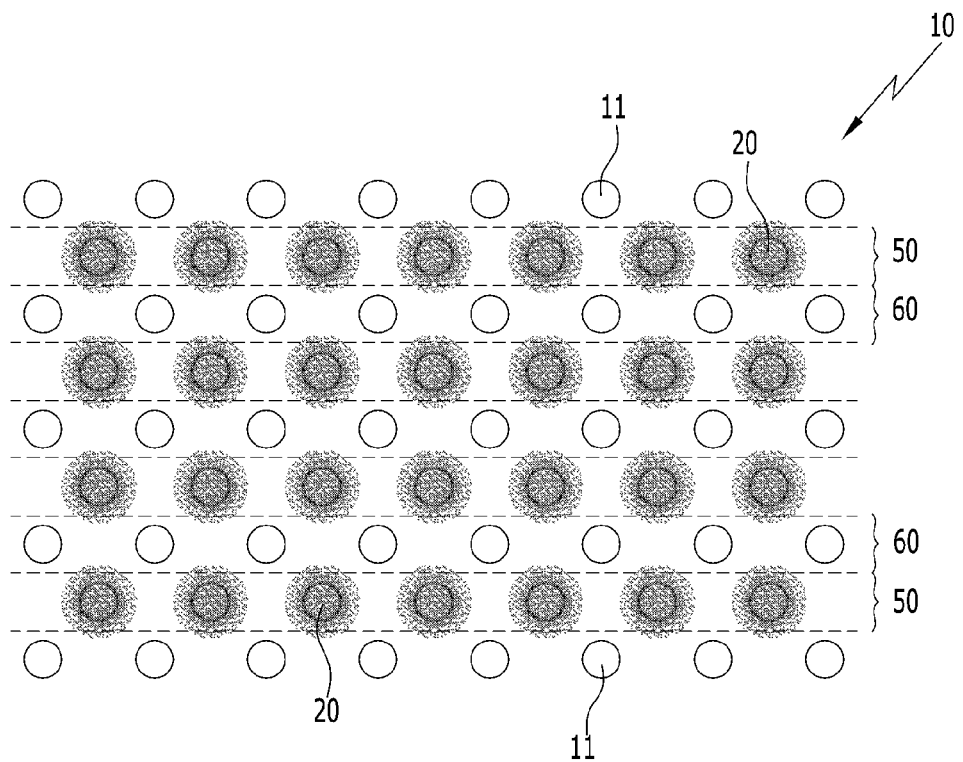
FIG. 8 is a cross-sectional view illustrating an antimicrobial filter using an optical fiber layer according to an embodiment of the present invention.
Figure 9:
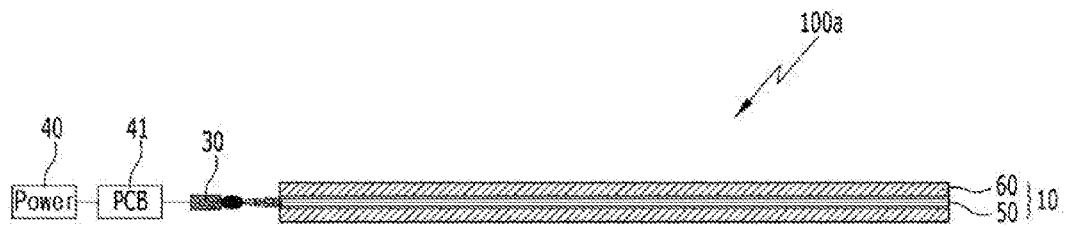
FIG. 9 is a side view illustrating an antimicrobial filter using an optical fiber layer according to an embodiment of the present invention.
Figure 10:
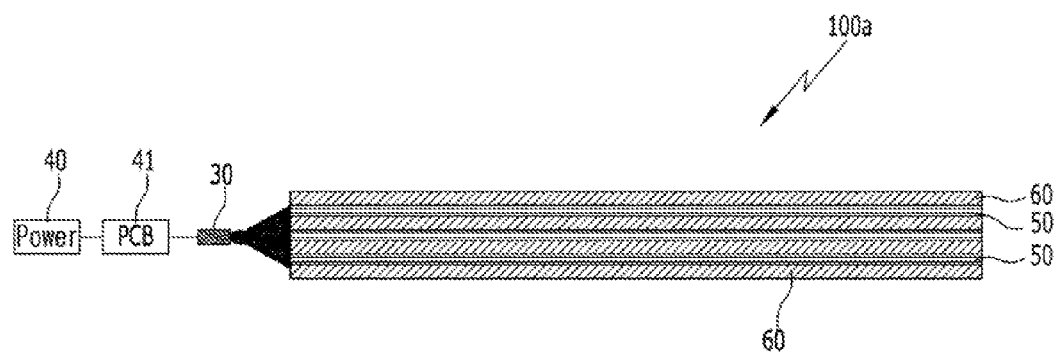
FIG. 10 is a side view illustrating an antimicrobial filter using a multilayered optical fiber layer according to an embodiment of the present invention.
Figure 11:
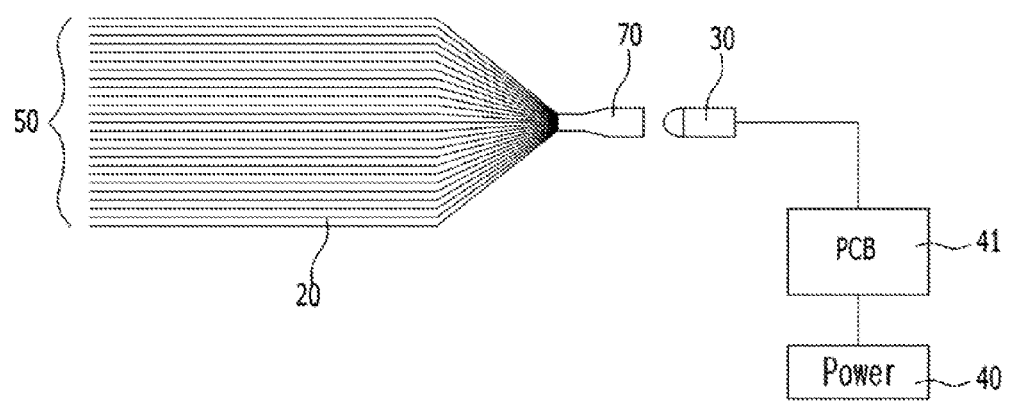
FIG. 11 is a schematic view illustrating an antimicrobial filter using an optical fiber layer according to an embodiment of the present invention.
Figure 12:
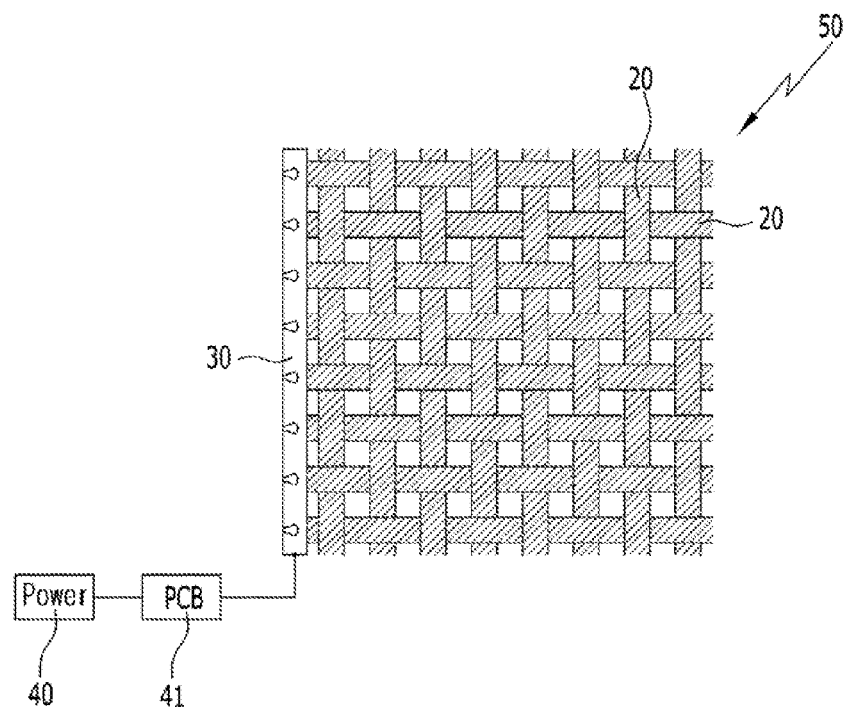
FIG. 12 is a plan view illustrating an antimicrobial filter having an optical fiber layer in an optical fiber fabric form according to an embodiment of the present invention.
Figure 13:
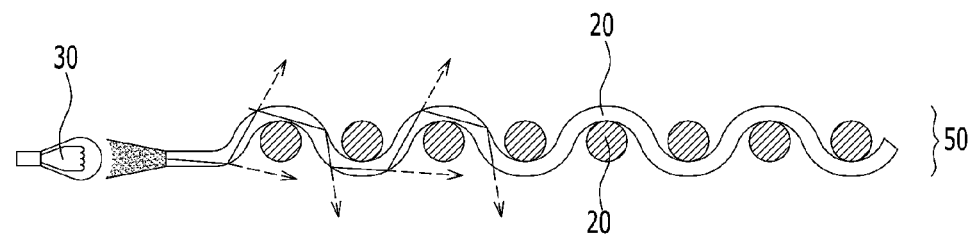
FIG. 13 is a schematic view illustrating the cross-section of FIG. 12.

FIG. 8 is a cross-sectional view illustrating an antimicrobial filter using an optical fiber layer according to an embodiment of the present invention, FIG. 9 is a side view illustrating an antimicrobial filter using an optical fiber layer according to an embodiment of the present invention, FIG. 10 is a side view illustrating an antimicrobial filter using a multilayered optical fiber layer according to an embodiment of the present invention, FIG. 11 is a schematic view illustrating an antimicrobial filter using an optical fiber layer according to an embodiment of the present invention, FIG. 12 is a plan view illustrating an antimicrobial filter having an optical fiber layer in an optical fiber fabric form according to an embodiment of the present invention, and FIG. 13 is a schematic view illustrating the cross-section of FIG. 12.

As illustrated in FIGS. 8 to 13, the antimicrobial filter 100A using an optical fiber layer according to the present invention comprises a filtration material 10 including an optical fiber layer 50 composed exclusively of optical fibers 20 in which a light source, which is received from one end of the optical fibers and travels in a longitudinal direction, is emittable through the surface of the optical fibers, and a filtration layer 60 for filtering particulate matter in air without including the optical fibers 20; a light source unit 30 for irradiating a light source to one end of the optical fibers 20 of the optical fiber layer 50; and a power supply 40 connected to the light source unit 30 to apply power so as to operate the light source.

As illustrated in FIGS. 8 to 12, the filtration material 10 includes an optical fiber layer(s) 50 and a filtration layer(s) 60, and the optical fiber layer 50 is a layer composed exclusively of a plurality of optical fibers 20. The optical fibers 20 remain the same as those described in reference to FIG. 5.

FIGS. 11 and 12 illustrate the antimicrobial filter using the optical fiber layer, wherein the depiction of the filtration layer 60 is omitted to efficiently show features of the optical fiber layer 50. As illustrated in FIGS. 12 and 13, the optical fiber layer 50 in an optical fiber fabric form may comprise a plurality of optical fibers 20 which are provided in the form of a fabric made with warp and weft. In this case, the optical fibers 20 are bent at positions where the weft optical fibers and the warp optical fibers cross each other, and thus light which is incident from the light source and travels through the inside of the optical fibers 20 may be emitted in a larger amount to the outside.

On the other hand, the filtration layer 60 is a porous layer without including the optical fibers, and may be a layer in the form of a woven fabric or nonwoven fabric composed of fibers 11. As such, the filtration layer 60 or the filtration material 10 composed of the optical fiber layer 50 and the filtration layer 60 may be coated with a photocatalyst. The photocatalyst may be synthesized using a variety of processes including a sol-gel process, etc., and may be applied on the filtration layer 60 and the filtration material 10 by spraying or coating. The photocatalyst may be exemplified by titanium dioxide ($TiO_2$), zinc oxide (ZnO), tungsten oxide ($WO_3$), etc., and may include any material which is activated by UV light, visible light or mixed light thereof so as to kill harmful microorganisms.

As illustrated in FIGS. 9 and 10, the light source unit 30 is a device for producing a light source which is to be irradiated to one end of the optical fibers 20 of the filtration material 10. Although a variety of devices may be provided, in the present invention, the light source unit 30 is connected to PCB (Printed Circuit Board) to thus control the light source. The light source irradiation by the light source unit 30 is typically known and thus an additional description for functions and structures thereof is omitted.

The light source may be any one selected from among visible light, UV light and natural light, and also one or more of them may be simultaneously applied.

Even when the irradiation time of the light source is set to within 1 hr per day to prevent breakage of the polymer of the filtration material 10 due to the long-term use of the light source, sufficient disinfecting effects may be attained.

As illustrated in FIGS. 9 and 10, the power supply 40 is connected to the light source unit 30 to apply power so as to operate the light source, and is connected to the PCB 41 to supply the produced power to the PCB 41.

Figure 14:
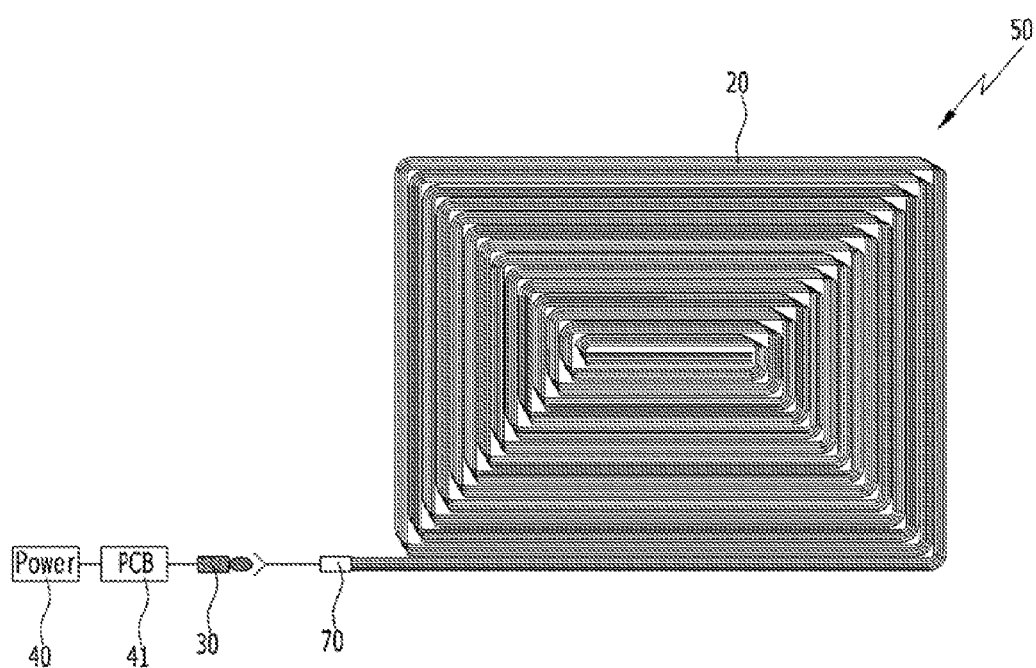
FIG. 14 is a schematic view illustrating an antimicrobial filter having an optical fiber layer using optical fibers connected over the entire surface thereof according to another embodiment of the present invention.

FIG. 14 schematically illustrates an antimicrobial filter having an optical fiber layer using optical fibers connected over the entire surface thereof according to another embodiment of the present invention.

As illustrated in FIG. 14, the antimicrobial filter using the optical fiber layer according to the present invention is formed to have the same structure, construction and configuration as in the antimicrobial filter using the optical fiber layer described in the above embodiment. As such, the antimicrobial filter according to another embodiment further includes a connector 70 which is connected to the light source unit 30 so as to connect one end of the optical fibers 20 of the optical fiber layer 50 and the light source unit, as in FIG. 11.

Also, FIG. 14 shows an optical fiber layer 50 in another configuration. To efficiently show the features of the optical fiber layer 50, the depiction of the filtration layer 60 is omitted in the drawing. The optical fiber layer 50 according to the present embodiment may include at least one optical fiber 20 continuously connected over the entire area of the optical fiber layer 50, more preferably a plurality of optical fibers 20 one end of which is connected to the connector 70.

Like this, FIG. 14 exemplarily illustrates the optical fiber layer 50 wherein optical fibers 20 spirally extend toward the center of the optical fiber layer 50 while being provided in the form of continuously smaller rectangles, but the optical fiber layer 50 need not be limited thereto and may be configured such that continuously extending optical fibers 20 are arranged in a zigzag pattern or are arranged so as to partially cross each other. Although the connector 70 is not specifically depicted herein, it may have a variety of forms which enable a light source emitted from the light source unit 30 to be effectively incident.

The other constructions are the same as in the above embodiment and an additional description thereof is omitted.

Figure 15:
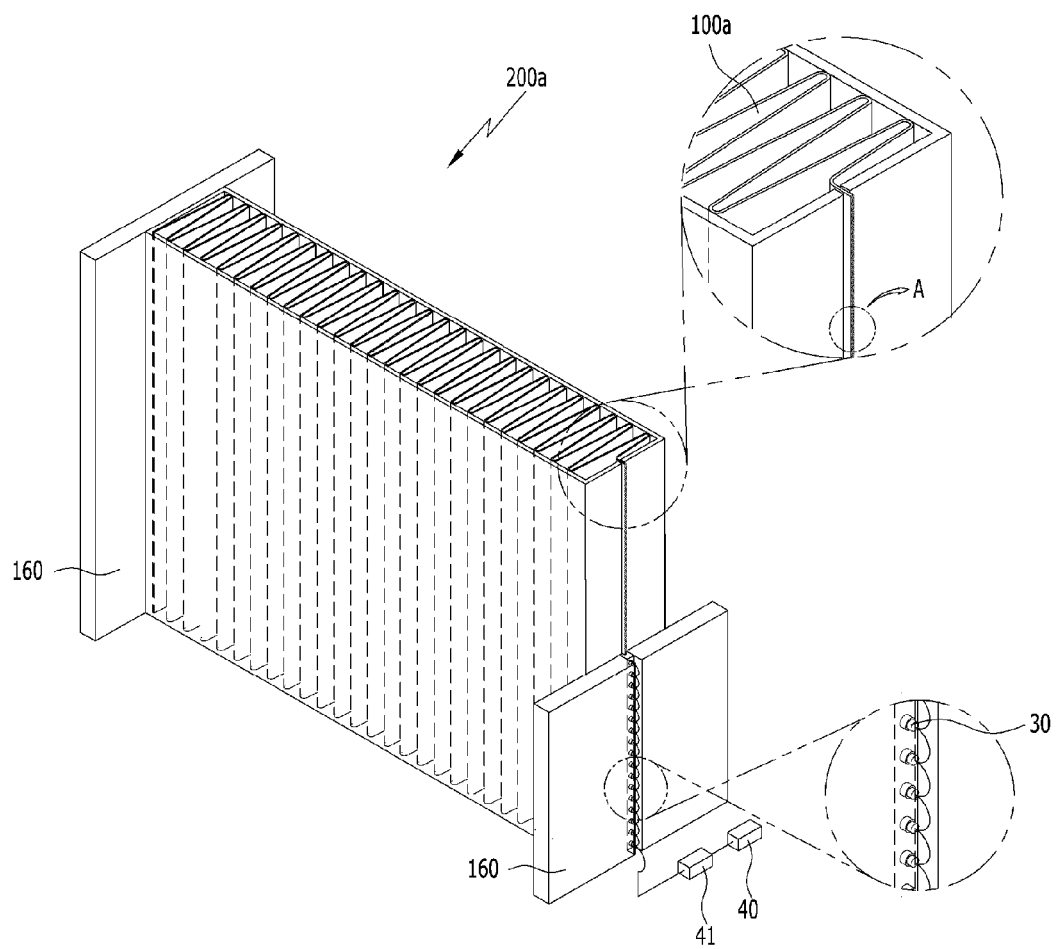
FIG. 15 is a schematic view illustrating an air cleaner including the antimicrobial filter having an optical fiber layer according to an embodiment of the present invention.
Figure 16:
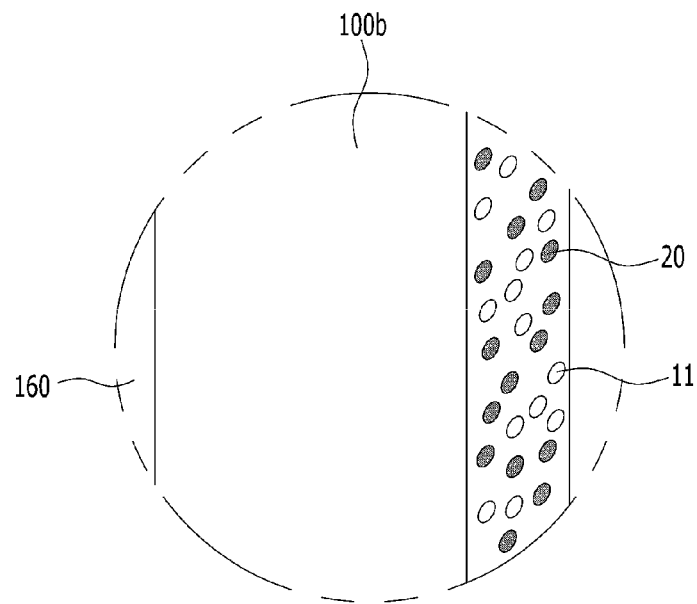
FIG. 16 is an enlarged view of Portion A of FIG. 15.
Figure 17:
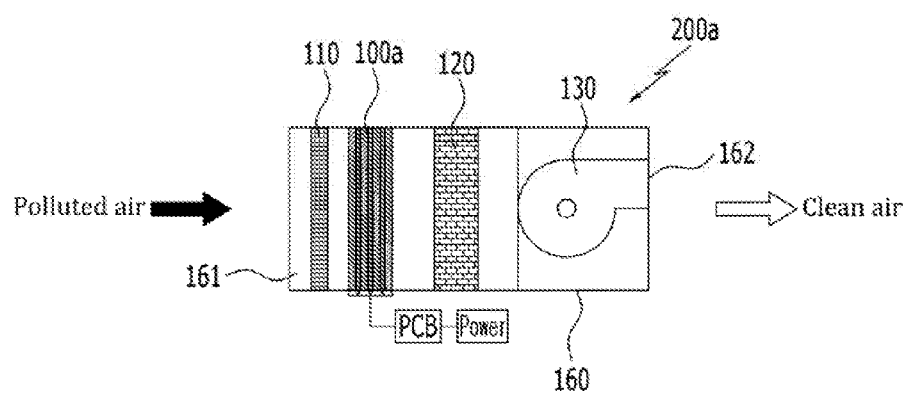
FIG. 17 is a schematic view illustrating an air cleaner including an antimicrobial filter having an optical fiber layer according to a first embodiment of the present invention.
Figure 18:
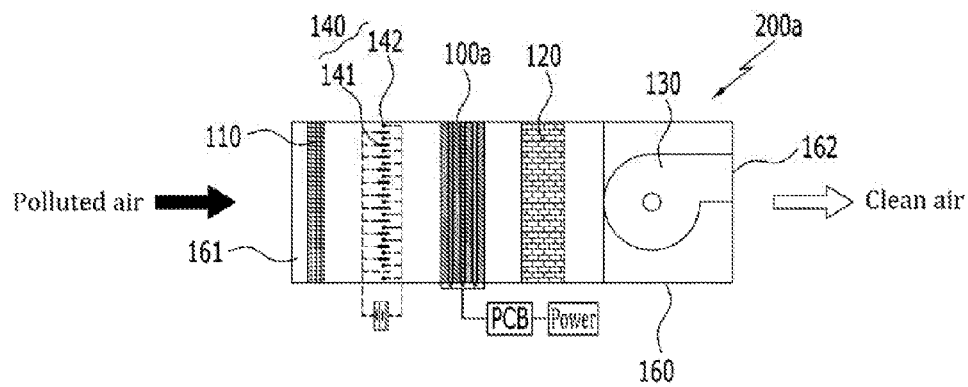
FIG. 18 is a schematic view illustrating an air cleaner including an antimicrobial filter having an optical fiber layer according to a second embodiment of the present invention.
Figure 19:
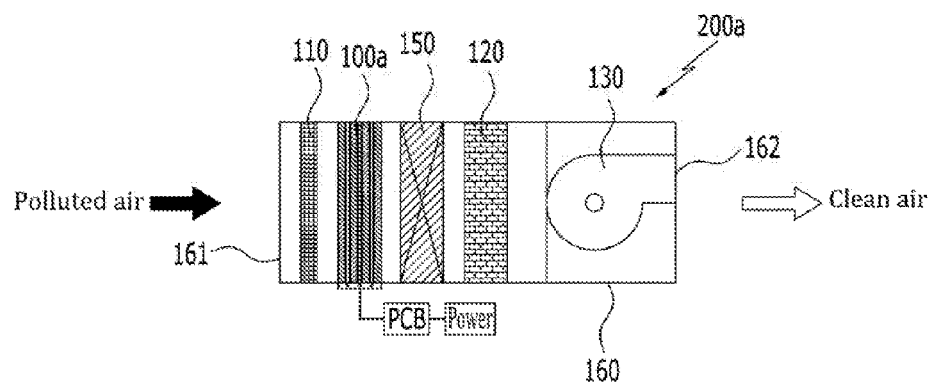
FIG. 19 is a schematic view illustrating an air cleaner including an antimicrobial filter having an optical fiber layer according to a third embodiment of the present invention.

FIG. 15 is a schematic view illustrating an air cleaner including the antimicrobial filter using an optical fiber layer according to an embodiment of the present invention, FIG. 16 is an enlarged view of Portion A of FIG. 15, FIG. 17 is a schematic view illustrating an air cleaner including an antimicrobial filter using an optical fiber layer according to a first embodiment of the present invention, FIG. 18 is a schematic view illustrating an air cleaner including an antimicrobial filter using an optical fiber layer according to a second embodiment of the present invention, and FIG. 19 is a schematic view illustrating an air cleaner including an antimicrobial filter using an optical fiber layer according to a third embodiment of the present invention.

As illustrated in FIGS. 17 to 19, the air cleaner 200A according to the present invention is an air cleaner 200A including the antimicrobial filter 100A using the optical fiber layer as described above, wherein the antimicrobial filter 100A is inserted into the duct case 160 of the air cleaner 200A, and the light source unit 30 and the power supply 40 are provided at one end of the antimicrobial filter 100A, that is, the lateral side of the duct case 160 of the air cleaner 200A.

The antimicrobial filter 100A of the air cleaner 200A is provided in the form of a pleated filter having a "∧ ∧ ∧" shape in order to increase the filtration area. This is merely illustrative, and various design modifications thereof are possible.

As illustrated in FIG. 17, the air cleaner 200A includes a duct case 160 comprising an inlet 161 through which polluted air is introduced to the inside and an outlet 162 through which the filtered clean air is discharged, a pretreatment filter 110 disposed near the inlet 161 of the duct case 160 so as to primarily filter the polluted air, the antimicrobial filter 100A according to the present invention disposed after the pretreatment filter 110 so as to filter fine dust in the polluted air, an adsorption filter 120 disposed after the antimicrobial filter 100A so as to adsorb and filter volatile organic compounds (VOCs) and offensive odors from the air, and an air blower 130 disposed after the adsorption filter 120 so as to transport the filtered clean air.

As such, as illustrated in FIG. 18, the air cleaner 200A according to the second embodiment may further include a charging device 140 between the pretreatment filter 110 and the antimicrobial filter 100A so as to electrically charge impurities in the air.

The charging device 140 may be subjected to corona discharge or electrospraying. The charging device 140 subjected to corona discharge includes ground electrodes 141 and discharge electrodes 142 so that corona discharge is generated by power supplied from an external power supply. The ground electrodes 141 which are in a flat plate form are spaced apart from each other, and the discharge electrodes 142 are disposed in the form of metal wires, metal needles, carbon fibers, etc. between the ground electrodes 141.

As illustrated in FIG. 19, the air cleaner 200A further includes a high-performance filter 150 such as a HEPA (High Efficiency Particulate Air) filter or a ULPA (Ultra Low Penetration Air) filter between the antimicrobial filter 100A according to the first embodiment and the adsorption filter 120.

The high-performance filter 150 plays a role in further filtering impurities such as very fine dust, etc., which are not filtered by the antimicrobial filter 100A, and the resulting air cleaner 200A may be applied to air conditioners for buildings, industrial sites or clean rooms of hospitals.

Figure 20:
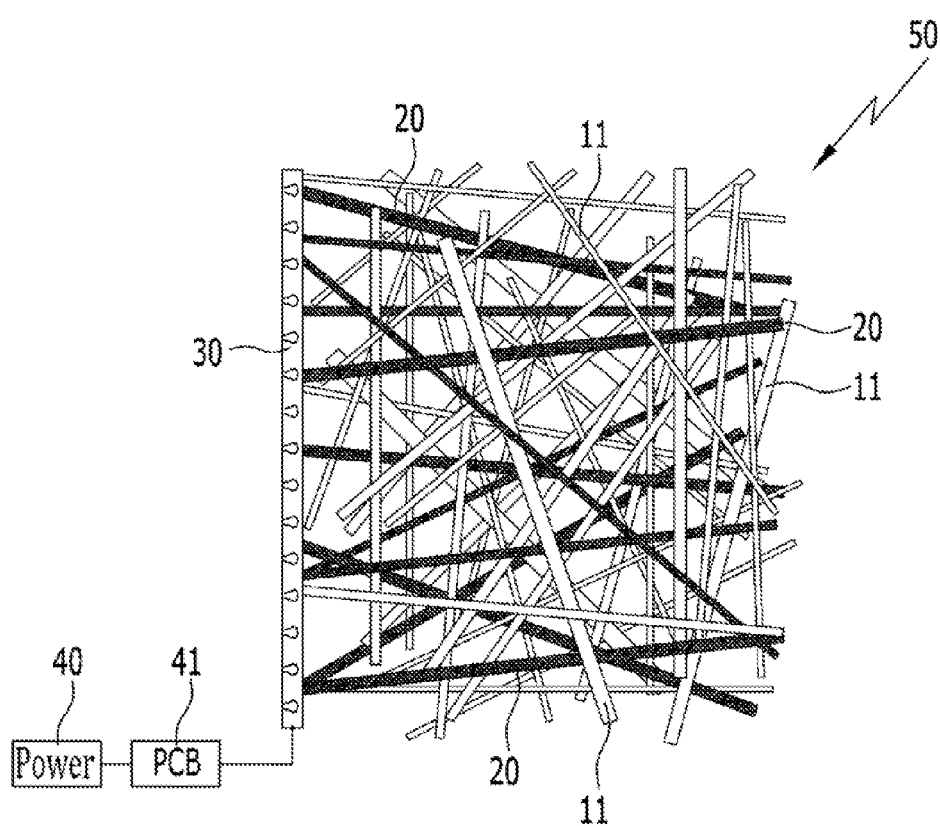
FIG. 20 is a plan view illustrating an antimicrobial filter using an optical fiber-mixed nonwoven fabric according to an embodiment of the present invention.
Figure 21:
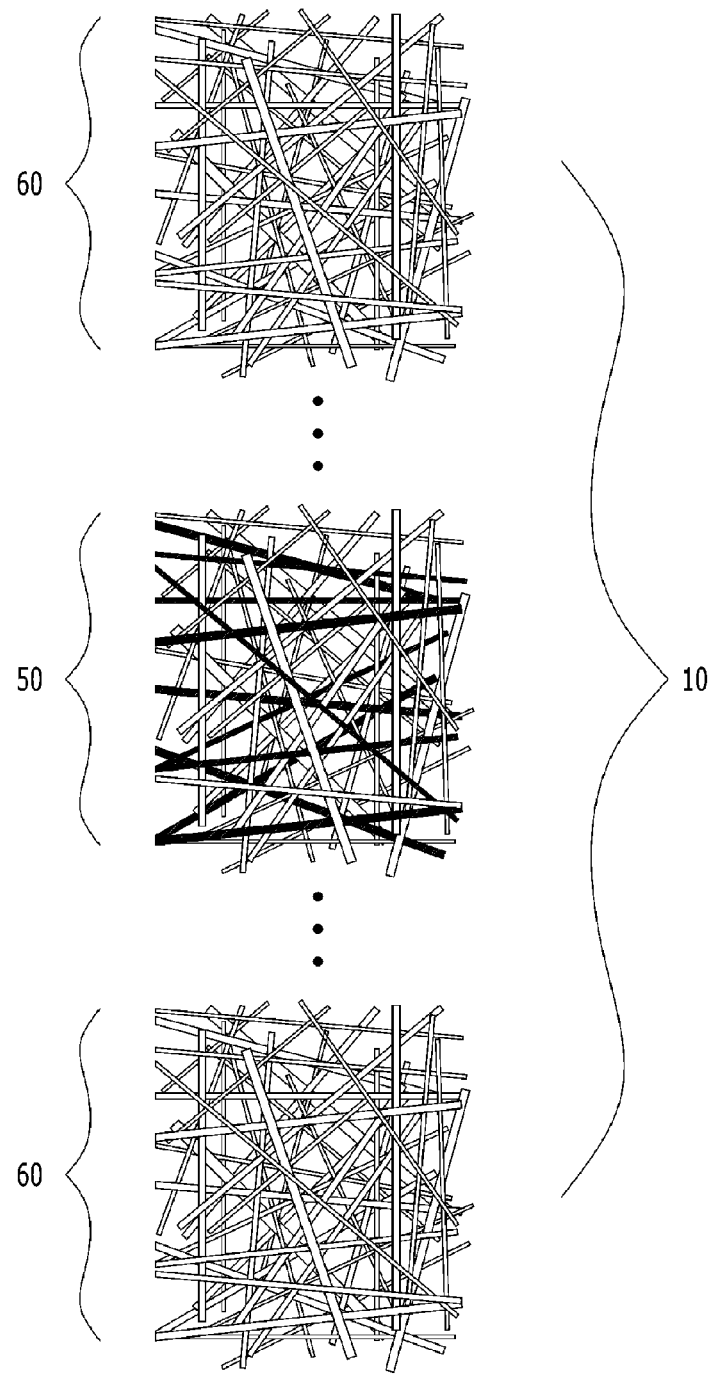
FIG. 21 is an exploded plan view illustrating the antimicrobial filter using an optical fiber-mixed nonwoven fabric according to the embodiment of the present invention.
Figure 22:
FIG. 22 is a side view illustrating an antimicrobial filter using an optical fiber-mixed nonwoven fabric according to an embodiment of the present invention.
Figure 23:
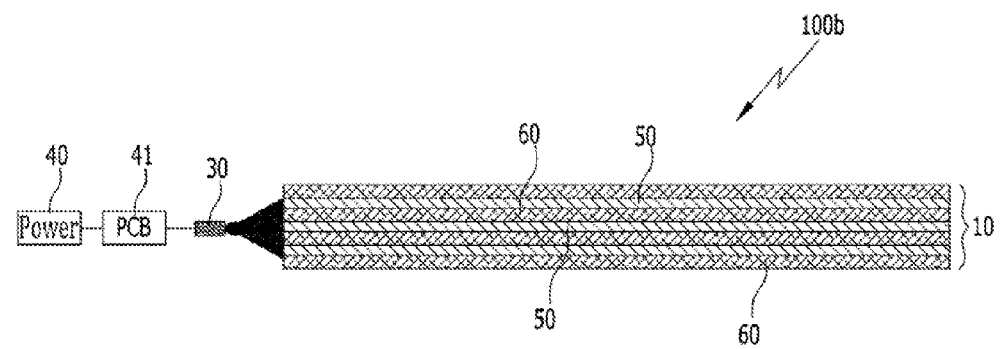
FIG. 23 is a side view illustrating an antimicrobial filter using a multilayered optical fiber-mixed nonwoven fabric according to an embodiment of the present invention.

FIG. 20 is a plan view illustrating an antimicrobial filter using an optical fiber-mixed nonwoven fabric according to an embodiment of the present invention, FIG. 21 is an exploded plan view illustrating the antimicrobial filter using an optical fiber-mixed nonwoven fabric according to the embodiment of the present invention, FIG. 22 is a side view illustrating an antimicrobial filter using an optical fiber-mixed nonwoven fabric according to an embodiment of the present invention, and FIG. 23 is a side view illustrating an antimicrobial filter using a multilayered optical fiber-mixed nonwoven fabric according to an embodiment of the present invention.

As illustrated in FIGS. 20 to 23, the antimicrobial filter 100B using an optical fiber-mixed nonwoven fabric according to the present invention includes an optical fiber-mixed nonwoven fabric 50 formed by irregularly mixing general nonwoven fibers 11 with optical fibers 20 in which a light source, which is received from one end of the optical fibers and travels in a longitudinal direction, is emittable through the surface of the optical fibers; a light source unit 30 for irradiating a light source to one end of the optical fiber-mixed nonwoven fabric 50; and a power supply 40 connected to the light source unit 30 to apply power so as to operate the light source.

As illustrated in FIGS. 20 to 23, the optical fiber-mixed nonwoven fabric 50 is a nonwoven fabric configured such that a plurality of fibers 11 and a plurality of optical fibers 20 for emitting light from the surface thereof therebetween are irregularly arranged. The plurality of fibers 11 may be typical synthetic fibers.

Moreover, the optical fiber-mixed nonwoven fabric 50 may be coated with a photocatalyst. The photocatalyst may be synthesized using a variety of processes including a sol-gel process, etc., and may be applied on the optical fiber-mixed nonwoven fabric 50 by spraying or coating. The photocatalyst may be exemplified by titanium dioxide ($TiO_2$), zinc oxide (ZnO), tungsten oxide ($WO_3$), etc., and may include any material which is activated by UV light, visible light or mixed light thereof so as to kill harmful microorganisms.

As illustrated in FIGS. 21 to 23, a filtration layer(s) 60 for filtering particulate matter in air and composed of a plurality of fibers 11 without including the optical fibers 20 is stacked on the top or bottom of an optical fiber-mixed nonwoven fabric(s) 50, thus constituting a filtration material 10.

The filtration material 10 may be configured such that a plurality of optical fiber-mixed nonwoven fabrics 50 and a plurality of filtration layers 60 are alternately stacked, as in FIG. 23.

Also, a connector (not shown) is further provided so as to connect one end of the optical fiber-mixed nonwoven fabric 50 and the light source unit 30.

Furthermore, the optical fibers 20 according to the present embodiment remain the same as those described in reference to FIG. 5.

As illustrated in FIGS. 20 to 23, the light source unit 30 is a device for producing a light source which is to be irradiated to one end of the optical fiber-mixed nonwoven fabric 50. Although a variety of devices may be provided, in the present invention, the light source unit 30 is connected to PCB (Printed Circuit Board) 41 to thus control the light source. The light source irradiation by the light source unit 30 is typically known and functions and structures thereof are not additionally described.

The light source may be any one selected from among visible light, UV light and natural light, and one or more of them may be simultaneously used.

Even when the irradiation time of the light source is set to within 1 hr per day to prevent breakage of the polymer of the optical fiber-mixed nonwoven fabric 50 due to the long-term use of the light source, sufficient disinfecting effects may be obtained.

As illustrated in FIGS. 20 to 23, the power supply 40 is connected to the light source unit 30 to apply power so as to operate the light source, and is connected to the PCB 41 so that the produced power is supplied to the PCB 41.

Figure 24:
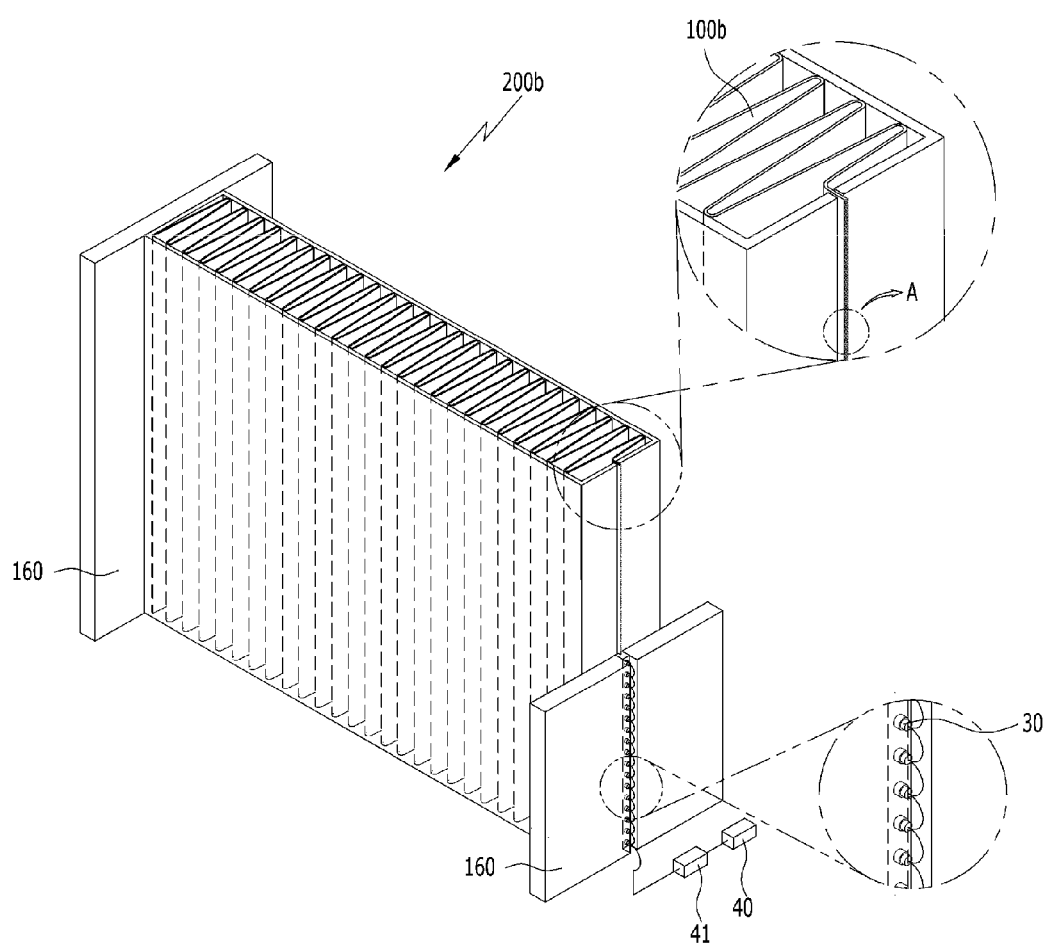
FIG. 24 is a schematic view illustrating an air cleaner including the antimicrobial filter using an optical fiber-mixed nonwoven fabric according to an embodiment of the present invention.
Figure 25:
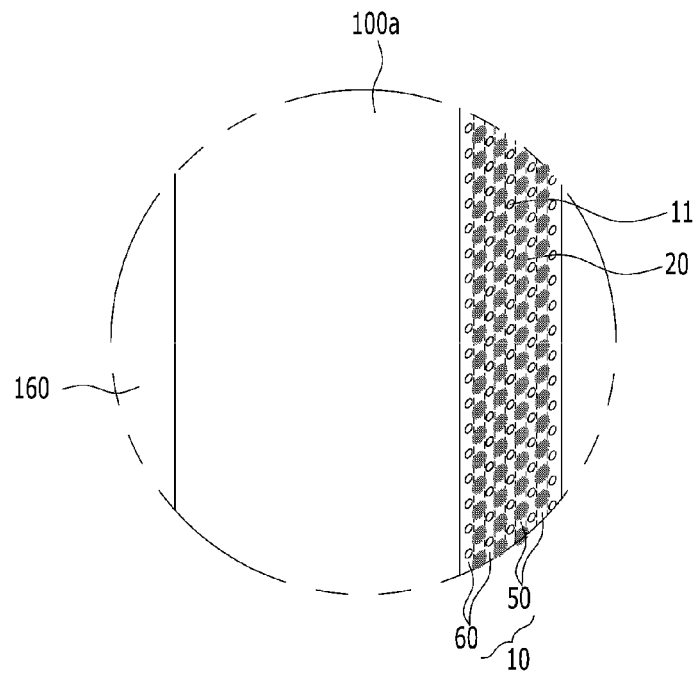
FIG. 25 is an enlarged view of Portion A of FIG. 24.
Figure 26:
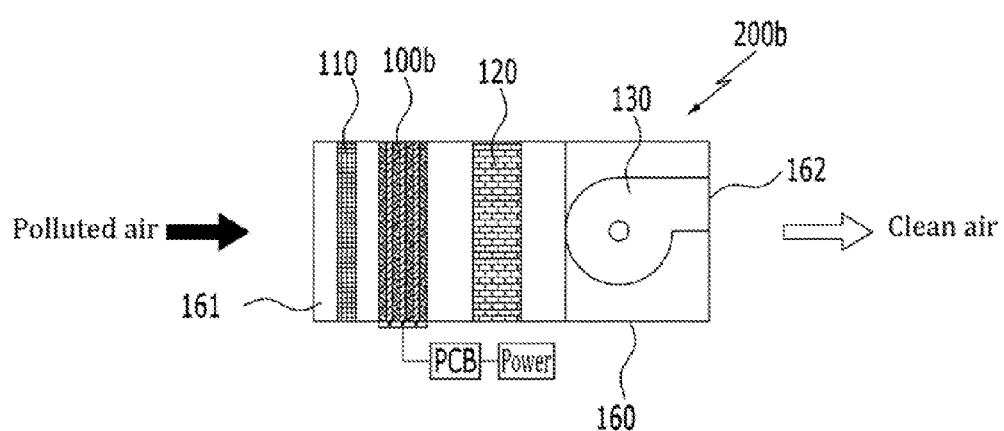
FIG. 26 is a schematic view illustrating an air cleaner including an antimicrobial filter using an optical fiber-mixed nonwoven fabric according to a first embodiment of the present invention.
Figure 27:
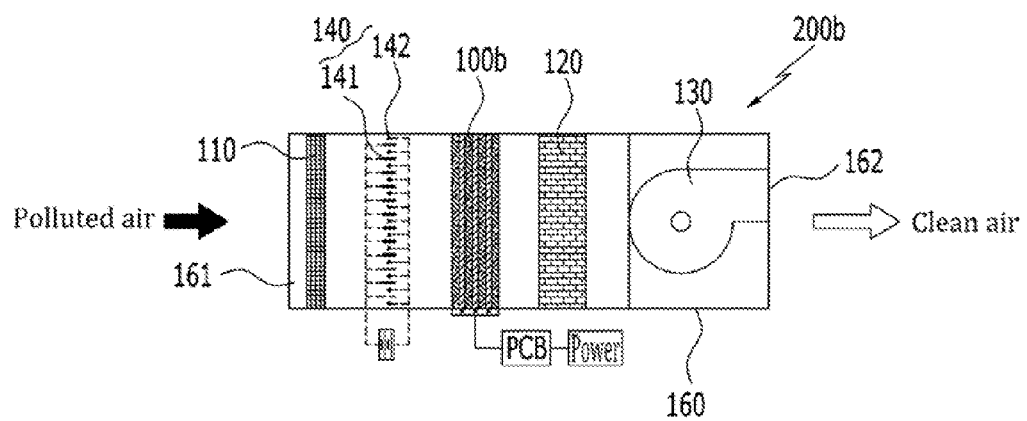
FIG. 27 is a schematic view illustrating an air cleaner including an antimicrobial filter using an optical fiber-mixed nonwoven fabric according to a second embodiment of the present invention.
Figure 28:
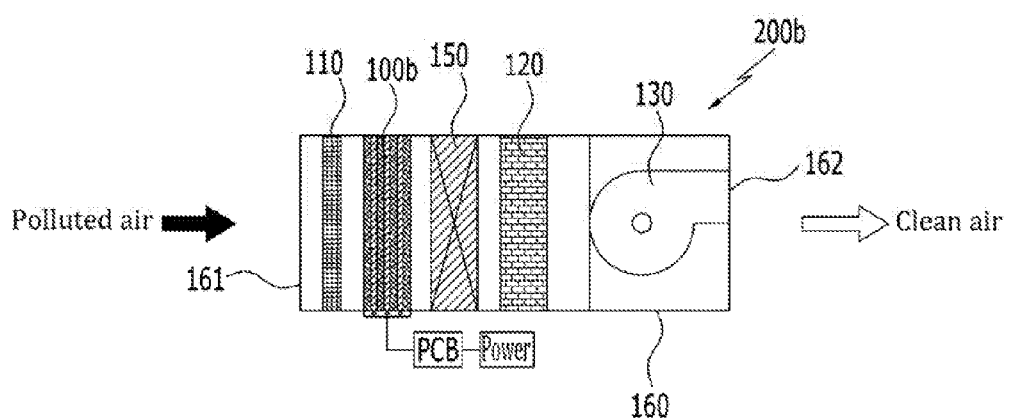
FIG. 28 is a schematic view illustrating an air cleaner including an antimicrobial filter using an optical fiber-mixed nonwoven fabric according to a third embodiment of the present invention.

FIG. 24 is a schematic view illustrating an air cleaner including the antimicrobial filter using an optical fiber-mixed nonwoven fabric according to an embodiment of the present invention, FIG. 25 is an enlarged view of Portion A of FIG. 24, FIG. 26 is a schematic view illustrating an air cleaner including an antimicrobial filter using an optical fiber-mixed nonwoven fabric according to a first embodiment of the present invention, FIG. 27 is a schematic view illustrating an air cleaner including an antimicrobial filter using an optical fiber-mixed nonwoven fabric according to a second embodiment of the present invention, and FIG. 28 is a schematic view illustrating an air cleaner including an antimicrobial filter using an optical fiber-mixed nonwoven fabric according to a third embodiment of the present invention.

As illustrated in FIGS. 24 to 28, the air cleaner including the antimicrobial filter using the optical fiber-mixed nonwoven fabric according to the present invention is an air cleaner 200B including the antimicrobial filter 100B using the optical fiber-mixed nonwoven fabric as described above, wherein the antimicrobial filter 100B is inserted into the duct case 160 of the air cleaner 200B, and the light source unit 30 and the power supply 40 are provided at one end of the antimicrobial filter 100B, namely, the lateral side of the duct case 160 of the air cleaner 200B.

As such, the antimicrobial filter 100B in the air cleaner 200B is provided in the form of a pleated filter having a "∧ ∧ ∧" shape in order to increase the filtration area. This is merely illustrative, and various design modifications thereof are possible.

As illustrated in FIG. 26, the air cleaner 200B includes a duct case 160 comprising an inlet 161 through which polluted air is introduced to the inside and an outlet 162 through which the filtered clean air is discharged, a pretreatment filter 110 disposed near the inlet 161 of the duct case 160 so as to primarily filter the polluted air, the antimicrobial filter 100B according to the present invention disposed after the pretreatment filter 110 so as to filter fine dust in the polluted air, an adsorption filter 120 disposed after the antimicrobial filter 100B so as to adsorb and filter volatile organic compounds (VOC) and offensive odors from the air, and an air blower 130 disposed after the adsorption filter 120 so as to transport the filtered clean air.

As such, as illustrated in FIG. 27, the air cleaner 200B according to the second embodiment further includes a charging device 140 between the pretreatment filter 110 and the antimicrobial filter 100B so as to electrically charge impurities in air.

The charging device 140 may be subjected to corona discharge or electrospraying. The charging device 140 subjected to corona discharge includes ground electrodes 141 and discharge electrodes 142 so that corona discharge is generated by power supplied from an external power supply. The ground electrodes 141, which are in a flat plate form, are spaced apart from each other, and the discharge electrodes 142 are disposed in the form of metal wires, metal needles, carbon fibers, etc. between the ground electrodes 141.

As illustrated in FIG. 28, the air cleaner 200B further includes a high-performance filter 150 such as a HEPA (High Efficiency Particulate Air) filter or a ULPA (Ultra Low Penetration Air) filter between the antimicrobial filter 100B according to the first embodiment and the adsorption filter 120.

The high-performance filter 150 functions to further filter impurities such as very fine dust, etc., which are not filtered by the antimicrobial filter 100B, and the resulting air cleaner 200B may be applied to air conditioners for buildings, industrial sites or clean rooms of hospitals.

The invention claimed is:

1. An antimicrobial filter using optical fibers, comprising:
a filtration material having contained therein one or more optical fibers in which a portion of a light source, which is received from one end of the optical fibers and travels in a longitudinal direction, is emitted through a surface of the optical fibers, the filtration material having a porous structure with air permeability in a thickness direction and filtering particulate matter in air;
a light source unit for irradiating said light source to said one end of the optical fibers of the filtration material; and
a power supply connected to the light source unit to apply power so as to operate the light source wherein the filtration material comprises an optical fiber layer composed exclusively of optical fibers in which a light source, which is received from one end of the optical fibers and travels in a longitudinal direction, is emittable through a surface of the optical fibers, and a filtration layer for filtering particulate matter in air without including the optical fibers.

2. The antimicrobial filter of claim 1, further comprising:
a connector for connecting one end of the optical fibers of the optical fiber layer and the light source unit.

3. The antimicrobial filter of claim 1, wherein the filtration material is configured such that a plurality of optical fiber layers and a plurality of filtration layers are alternately stacked.

4. An antimicrobial filter using optical fibers, comprising:
an optical fiber-mixed nonwoven fabric formed by irregularly mixing general fibers with optical fibers in which a light source, which is received from one end of the optical fibers and travels in a longitudinal direction, is emittable through a surface of the optical fibers;
a light source unit for irradiating said light source to one end of the optical fiber-mixed nonwoven fabric to illuminate said one end of said optical fibers; and
a power supply connected to the light source unit to apply power so as to operate the light source further comprising a filtration layer formed so as to be stacked on the optical fiber-mixed nonwoven fabric and for filtering particulate matter in air and composed of a plurality of fibers without including the optical fibers.

5. The antimicrobial filter of claim 1, wherein the light source is a lamp or LED.

6. The antimicrobial filter of claim 1, wherein the light source is in a package form in which a plurality of light sources is aligned.

7. An air cleaner, comprising the antimicrobial filter of claim 1.

8. The antimicrobial filter of claim 4, wherein the light source is a lamp or LED.

9. The antimicrobial filter of claim 4, wherein the light source is in a package form in which a plurality of light sources is aligned.

* * * * *